United States Patent

Roman et al.

[11] Patent Number: 5,556,276
[45] Date of Patent: Sep. 17, 1996

[54] LASER ANNEALING MARKING OF ORTHODONTIC APPLIANCE

[75] Inventors: Patrick Roman, Escondido, Calif.; Orlan Hayes, Orlando, Fla.

[73] Assignee: Lancer Orthodontics, Inc., San Marco, Calif.

[21] Appl. No.: 327,733

[22] Filed: Oct. 24, 1994

[51] Int. Cl.⁶ .................................................. A61C 7/12
[52] U.S. Cl. .................................................. 433/8; 433/23
[58] Field of Search ............................... 433/8, 9, 22, 23

[56] References Cited

U.S. PATENT DOCUMENTS

| | | | |
|---|---|---|---|
| 5,238,402 | 8/1993 | Röhlcke et al. | 433/8 |
| 5,322,436 | 6/1994 | Horng et al. | 433/23 |

OTHER PUBLICATIONS

"Industrial Strength Laser Marking: Turning Photons Into Dollars," Richard L. Stevenson, Marketing Director, Excel/Control Laser, 1992 (Brochure).

*Primary Examiner*—David A. Wiecking
*Attorney, Agent, or Firm*—Fulwider Patton Lee & Utecht

[57] ABSTRACT

An orthodontic appliance for use in the mouth which includes an annealing process to provide a marking area. A laser is used to surface anneal an orthodontic appliance, such as an orthodontic bracket, for identification purposes and to withstand a number of recycling processes for sterilization purposes. The surface annealing process does not remelt the marking area and is an advantage over the prior art in that the marking area is not rough or weakened by remelting the structure.

27 Claims, 1 Drawing Sheet

LASER ANNEALING MARKING OF ORTHODONTIC APPLIANCE

FIELD OF THE INVENTION

The invention relates generally to identifying orthodontic appliances. More specifically, the invention relates to marking orthodontic appliances and tools for easy identification by orthodontists.

BACKGROUND OF THE INVENTION

The field of orthodontics is fairly well defined as to the movement of teeth and the time periods required to effect certain movements. During the treatment process the orthodontist will normally have in mind the types of orthodontic appliances she intends to use, however, specific sizes of appliances are dictated by each individual patient. For example, when fitting a patient for orthodontic brackets, the orthodontist must select from any number of different sizes for each individual tooth in order to properly fit the patient. This is a trial and error process wherein the orthodontist will remove an orthodontic appliance from a tray provided by the manufacturer and place the orthodontic bracket on the tooth, without attaching it, so that the orthodontist can measure the size of the bracket in relation to the size of the tooth and to determine the proper angulation built into the bracket. If the orthodontist has incorrectly selected a particular orthodontic bracket, that bracket must be sterilized before being returned to the tray from which it came. The same trial and error process can occur for buccal tubes, bands, archwires and other appliances. Thus, at the end of a fitting, the orthodontist may be faced with dozens of orthodontic appliances which need to be sterilized and replaced to their respective trays. Also, any tools used in the mouth such as pliers, must be sterilized.

As a result of the sterilization process, the orthodontic appliances become commingled and are difficult to identify because of their small size and nearly identical shape. In order to more easily identify orthodontic appliances, various methods have been employed such as color coding portions of the appliance. Unfortunately, the color tends to wash away with the sterilization process leaving the orthodontist with the task of sorting through unmarked appliances.

Others have marked the orthodontic appliances by remelting a portion of the appliance such as described in U.S. Pat. No. 5,238,402 to Rohlcke et al. It is possible, due to the small size of the orthodontic appliances, that remelting will weaken the appliance and in any event it causes a roughened surface in the area of the remelt.

What has been needed and as yet been unavailable is a convenient method of marking an orthodontic appliance that will not wash away during sterilization and does not weaken or disrupt the surface of the orthodontic appliance such as in the Rohlcke et al. patent.

DESCRIPTION OF RELATED ART

There are numerous orthodontic appliances that can be marked using the annealing method of the present invention. Examples of such devices are found in U.S. Pat. Nos. 3,881,252 (bands); 3,660,900 (single wing bracket); 4,818,226 (mitinol archwire); 4,954,080 (ceramic bracket); 5,064,370 (crystalline alumina appliances); and 4,415,330 (orthodontic brackets, bands, and buccal tubes), all of which are incorporated herein by reference.

SUMMARY OF THE INVENTION

The present invention solves the marking problem by providing a permanent marking area on the surface of an orthodontic appliance that will not wash out during sterilization and does not remelt the surface so as to cause disruption or weaknesses in the appliance.

More specifically, an orthodontic appliance for use in the mouth has an outer surface which is annealed by a laser. The laser beam is of sufficient power to anneal the surface thereby causing a marking area on a portion of the surface, without remelting the surface area. The marking area is visible with the naked eye and will not wash out by conventional sterilization processes in an autoclave.

The annealing process using a laser to create a marking area can be carried out on most orthodontic appliances and tools including pliers, orthodontic brackets, buccal tubes, archwires, bands and so forth. Unlike the marking processes which remelt the surface area to provide a marking portion, the present invention can be used on surfaces other than metallic. As an example, the method of the present invention can be used to mark metallic surfaces, ceramics or plastics.

DETAILED DESCRIPTION OF THE PREFERRED EMBODIMENTS

Figure 1:
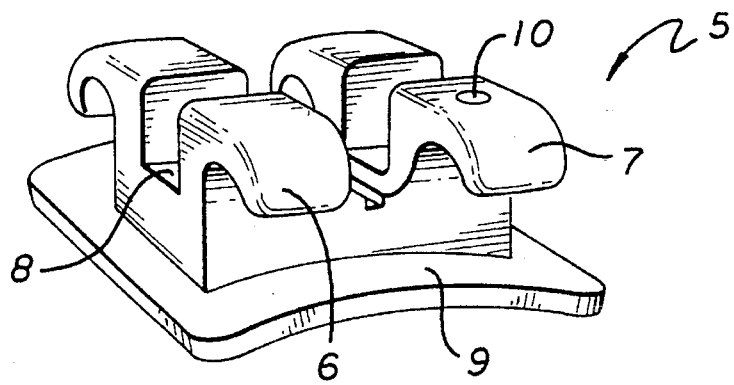
FIG. 1 is a perspective view of an orthodontic bracket embodying features of the invention including a portion having a marking area.

In keeping with the invention, in a preferred embodiment as depicted in FIG. 1, an orthodontic bracket 5 is depicted. The orthodontic bracket 5 is typical of the type of bracket used by orthodontists in applying corrective forces to the teeth. Generally, a pair of tie wings 6, 7 are mounted on a base pad 9 and have an archwire slot 8 bisecting tie wings 6 and 7. Base pad 9 is used as an interface between the orthodontic bracket and the patient's tooth and is commonly attached to the tooth by an adhesive that is well known in the art. Orthodontic bracket 5 may also be attached to a band (not shown) by known attachment means such as brazing, welding or the like. The band encircles a patient's tooth leaving the orthodontic bracket 5 projecting outwardly to receive an archwire (not shown). In a preferred embodiment, marking area 10 is provided on orthodontic bracket 5, and generally on one or both of tie wings 6, 7. Marking area 10 can include any specific pattern or design, or may include any combination of alpha and numeric characters for identification of orthodontic bracket 5. As an example, a single dot on the gingival portion of tie wing 6 may indicate that the bracket is to be attached to an upper left central tooth. As another example a single dot on the occlusal portion of tie wing 6 may indicate that the bracket is to be attached to a lower left bicuspid. Other configurations, designs or patterns could include circles, triangles, squares, lines, or virtually any type of pattern for identification purposes. Further, marking area 10 may include alpha and numeric characters which specifically identify each individual orthodontic bracket which corresponds to a specific tooth. As is commonly known in the art, various alpha numeric characters identify specific orthodontic brackets as are represented in Table 1. Such alpha numeric characters can be annealed into orthodontic bracket 5 and would be clearly visible under magnification.

TABLE 1

| UPPER | LOWER |
|-------|-------|
| UL1 | LL1 |
| UL2 | LL2 |
| UL3 | LL3 |
| UL4 | LL4 |
| UL5 | LL5 |
| UR1 | LR1 |
| UR2 | LR2 |
| UR3 | LR3 |
| UR4 | LR4 |
| UR5 | LR5 |

In keeping with the invention, marking area 10 is formed by an annealing process in which a portion of orthodontic bracket 5 is annealed such that the marking area 10 becomes discolored. The annealing process is actually an oxidation of the surface of the material being annealed. While annealing orthodontic bracket 5 in air will generally cause a dark or near black marking area 10 in metal, annealing in other gases will result in marking areas of different colors. Thus, marking area 10 can also be used to identify a particular bracket by not only the pattern, design or alpha numeric character, but by its color as well.

Figure 2:
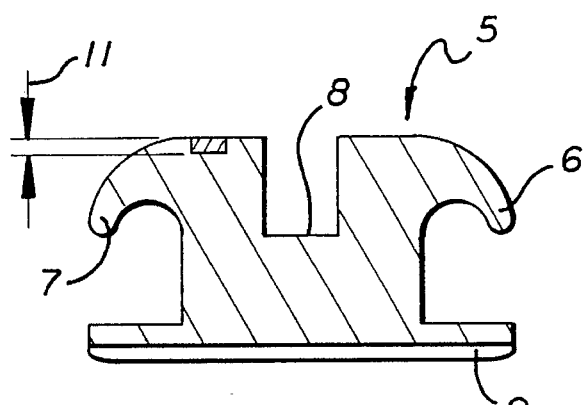
FIG. 2 is a cross-sectional view of the orthodontic bracket of FIG. 1 depicting the depth of the marking area.
Figure 3:
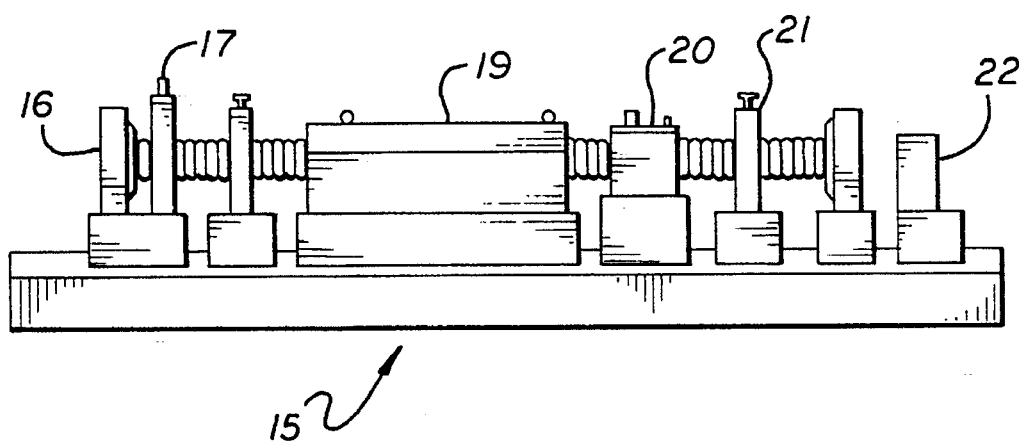
FIG. 3 is an elevational view of a typical laser used to surface anneal an orthodontic appliance to provide a marking area.

The depth of marking area 11 is depicted in FIG. 2 and is determined by a number of factors. As seen in FIG. 3, it is an aspect of the invention to use some form of laser to anneal the surface of orthodontic bracket 5 to thereby create marking area 10. The annealing process relies on heat conducting into the material, thus the laser beam velocity must be held comparatively slow. The velocity of the laser is one factor which determines depth of marking area 11. Other factors which will influence the depth of marking area 11 of orthodontic bracket 5 include thermoconductivity of the bracket, its color, and its surface finish. Factors relating to a typical laser's performance will also influence the depth of marking area 11, and include factors such as continuous or Q-switching modes of operation, peak power (in kilowatts), energy per pulse, pulse width, and beam diameter.

The laser depicted in FIG. 3 can include but is not limited to lasers identified as Nd:ELF, Nd:YAG and $CO_2$. Other lasers are commercially available for the annealing process which creates marking area 10. It is generally preferred to use lasers operating in the infrared wavelength range for annealing purposes. An excellent publication relating to laser technology for the purpose of annealing objects is entitled "Industrial Strength Laser Marking: Turning Photons into Dollars," and is published by Excel Control Laser of Orlando, Fla., which publication is incorporated by reference in its entirety. Common operating parameters are described in the brochure by Excel Control Laser that could be used for annealing orthodontic bracket 5. For example, typical performance specifications are found at page 14 of the brochure.

Typical performance specifications for laser annealing using a Nd:YAG laser are as follows:

| CW Performance | 15 watt TEMoo | 50 watt Multimode | 100 watt Multimode |
|---|---|---|---|
| CW Power (min.) (watts) | 8 | 50 | 100 |
| Instability (max.) (% RMS) | 3 | 3 | 3 |
| Beam Diameter @1/e2 (mm) | 1 | 4 | 6.5 |
| Beam Divergence @1/e2 (max.) (mr) | 2.5 | 10 | 10 |
| QS Performance @ 1 kHz | | | |
| Peak Power (min.) (kW) | 15 | 75 | 120 |
| Energy/Pulse (min.) (mJ) | 1.9 | 12 | 20 |
| Pulse Width (max.) (nsec) | 130 | 160 | 170 |
| Peak Power Instability (max.) (% p − p) | 6 | 8 | 15 |
| QS Performance @ 10 kHz | | | |
| Peak Power (min.) (kW) | 2.4 | 18 | |
| Energy/Pulse (min.) (mJ) | 0.6 | 4 | |
| Pulse Width (max.) (nsec) | 260 | 220 | |
| Peak Power Instability (max.) (% p — p) | 15 | 15 | |

While the foregoing laser settings are appropriate for annealing a marking area for the present invention, many other lasers and numerous settings operate in substantially the same way to accomplish the same function and result of the present invention. With respect to the Nd:YAG laser settings above: the "CW" refers to continuous wave performance (i.e., direct output); the "QS" refers to "Q-switch" mode of operation; and "TEMoo" refers to operation in the transverse electromagnetic mode to produce very narrow line widths. Further details of operation can be found in the Excel Control Laser publication referenced above.

Orthodontic bracket 5 can be formed from various materials including various combinations of stainless steel, ceramic or plastic. Since the annealing process does not actually melt orthodontic bracket 5 in the marking area 10, there is no surface irregularity nor are there any weakened points as a result of melting. Typical of orthodontic appliances having a remelted marking area is U.S. Pat. No. 5,238,402, which is incorporated herein by reference. Unlike the referenced patent, the annealing process of the present invention does not remelt the structure of the orthodontic appliance.

Marking area 10 is useful to orthodontists not only for identification purposes, but it will withstand sterilization and recycling processes used by orthodontists. In other words, once an orthodontic bracket 5 has been fitted to a patient's tooth and determined to be the wrong size, it must be sterilized before it can be used on another patient. The sterilization process, commonly known in the art, may remove an ordinary marking area which could be by a dye or other coloration process. The present invention provides a permanent marking area that will withstand a number of sterilization or recycling processes that are consistent with the total number any one bracket might be subjected to.

The present invention is not limited to annealing a marking area on orthodontic brackets, but can include marking orthodontic archwires, buccal tubes, bands, or other orthodontic appliances such as tools to be used in the mouth. Further, orthodontic brackets can be made from any type of stainless steel, ceramics, or plastics and are also receptive to a marking area 10 as described above. Examples of orthodontic brackets, archwires, buccal tubes, and bands, and various different materials such as stainless steel, ceramics and plastics can be found in the U.S. patents set forth above.

Other modifications and improvements can be made to the invention without departing from the scope thereof.

What is claimed is:

1. A method for surface treating an orthodontic appliance, comprising the steps of:

providing an orthodontic appliance having an outer surface;

marking a selected portion of said outer surface by applying a laser beam of sufficient power to anneal said selected portion, thereby causing the selected area to become visible on said outer surface, wherein said marking step does not create any surface irregularity on the outer surface.

2. The method of claim 3, wherein said marking step is performed without melting any portion of said orthodontic appliance.

3. An orthodontic appliance for use in the mouth, comprising an outer surface on said orthodontic appliance and a marking area on said outer surface provided by annealing said outer surface.

4. The orthodontic appliance of claim 3, wherein a laser is used for annealing said marking area, said laser is taken from the group of lasers consisting of Nd:ELF, Nd:YAG and $CO_2$.

5. The orthodontic appliance of claim 4, wherein said laser for surface annealing operates in a Q-switched mode with peak power ranging from 2.4 to 120 kw, the energy/pulse operating at 0.06 to 20 m, and the pulse width at 130 to 260 Sec.

6. The orthodontic appliance of claim 4, wherein said laser for surface annealing operates in a continuous mode with continuous power in the range of 8 to 100 watts, the beam diameter in the range of 1 to 6.5 mm, and the beam divergence in the range of 2.5 to 10 mr.

7. The orthodontic appliance of claim 4, wherein said laser is a 50 watt Nd:YAG laser operating at approximately 1.06 μm wavelength.

8. The orthodontic appliance of claim 3, wherein said outer surface on said orthodontic appliance is annealed without melting any portion of said outer surface.

9. The orthodontic appliance of claim 3, wherein said outer surface is comprised of stainless steel.

10. The orthodontic appliance of claim 3, wherein said outer surface is made from nitinol (NiTi).

11. The orthodontic appliance of claim 3, wherein said outer surface is made from ceramic.

12. The orthodontic appliance of claim 3, wherein said outer surface is made from plastic.

13. The orthodontic appliance of claim 3, wherein said appliance is taken from the group of appliances consisting of orthodontic brackets, bands, buccal tubes, and archwires.

14. The orthodontic appliance of claim 3, wherein said marking area formed by said annealing treatment has a thickness in the range of about 0.0001 to 0.001 inches.

15. The orthodontic appliance of claim 3, wherein said marking area includes, alone or in combination, a pattern, a specific design, and alpha and numeric characters.

16. A method for surface treating an orthodontic appliance, comprising:

providing an orthodontic appliance having an outer surface;

annealing said outer surface by applying a laser beam of sufficient power to cause a marking area to become visible on said outer surface.

17. The method of claim 16, wherein said laser is operated in a continuous mode.

18. The method of claim 16, wherein said laser is operated in a Q-switched mode.

19. The method of claim 16, wherein said annealing method step occurs in ambient air.

20. The method of claim 16, wherein said annealing step is performed without melting any portion of said orthodontic appliance.

21. The method of claim 16, wherein said annealing step oxidizes a portion of said outer surface to create said marking area.

22. The method of claim 16, wherein said marking area includes, alone or in combination, a pattern, a specific design, and alpha and numeric characters.

23. An orthodontic bracket for use in the mouth, comprising an outer surface on said orthodontic bracket, a marking area on said outer surface provided by annealing said outer surface using a laser operating in the infrared wavelength range.

24. A method for surface treating an orthodontic bracket, comprising:

providing an orthodontic bracket having an outer surface;

annealing said outer surface and oxidizing a marking area on said outer surface, said annealing step provided by a laser operating in the infrared wavelength range.

25. An orthodontic appliance for use in the mouth, comprising an outer surface on said orthodontic appliance and an annealed marking area on said outer surface, said annealed marking area having no surface disruptions.

26. The orthodontic appliance of claim 25, wherein said annealed marking area is annealed without melting any portion of said outer surface.

27. The orthodontic appliance of claim 25, wherein a laser is used for annealing said annealed marking area.

* * * * *

UNITED STATES PATENT AND TRADEMARK OFFICE
CERTIFICATE OF CORRECTION

PATENT NO.   : 5,556,276
DATED        : Sept. 17, 1996
INVENTOR(S)  : Patrick Roman, Orlan Hayes It is certified that error appears in the above-indentified patent and that said Letters Patent is hereby corrected as shown below:

Column 5, Claim 2, Line 12, change "claim 3", to read --claim 1--.

Signed and Sealed this

Seventh Day of October, 1997

Attest:

BRUCE LEHMAN

Attesting Officer

Commissioner of Patents and Trademarks